United States Patent [19]
Sato et al.

[11] Patent Number: 4,669,315
[45] Date of Patent: Jun. 2, 1987

[54] ROTATING MACHINERY DIAGNOSIS SYSTEM WITH ACOUSTIC EMISSION TECHNIQUE

[75] Inventors: Ichiya Sato, Hitachi; Takao Yoneyama, Katsuta, both of Japan

[73] Assignee: Hitachi, Ltd., Tokyo, Japan

[21] Appl. No.: 884,897

[22] Filed: Jul. 14, 1986

[30] Foreign Application Priority Data

Jul. 19, 1985 [JP] Japan ................... 60-158231

[51] Int. Cl.$^4$ ........................... G01N 29/04
[52] U.S. Cl. ........................................ 73/660
[58] Field of Search ................... 73/660, 593, 587

[56] References Cited
U.S. PATENT DOCUMENTS

| | | | |
|---|---|---|---|
| 4,377,947 | 3/1983 | Matsushita et al. | 73/660 |
| 4,453,407 | 6/1984 | Sato et al. | 73/660 |
| 4,478,082 | 10/1984 | Sato et al. | 73/660 |
| 4,481,819 | 11/1984 | Yoneyama et al. | 73/660 |

Primary Examiner—Anthony V. Ciarlante
Attorney, Agent, or Firm—Antonelli, Terry & Wands

[57] ABSTRACT

Disclosed is a rotating machinery diagnosis system with an AE technique, which comprises: an AE sensor mounted on a rotary machine for sensing an acoustic signal of the rotary machine; envelope detector means for obtaining an envelope signal from the acoustic signal from the AE sensor; waveform-feature processor means for performing signal processing so as to detect a feature of waveform of an output waveform signal from the envelope detector means; feature decision means for judging whether the feature of waveform belongs to a continuous type or a burst type and/or to a rotation-synchronous type or a rotation-asynchronous type on the basis of an output signal from the waveform-feature processor means; and diagnostic output means for outputting and displaying an output signal from the feature decision means, whereby it is possible to perform judgement simultaneously as to a plurality of kinds of abnormality.

9 Claims, 14 Drawing Figures

FR : ROTATIONAL FREQENCY

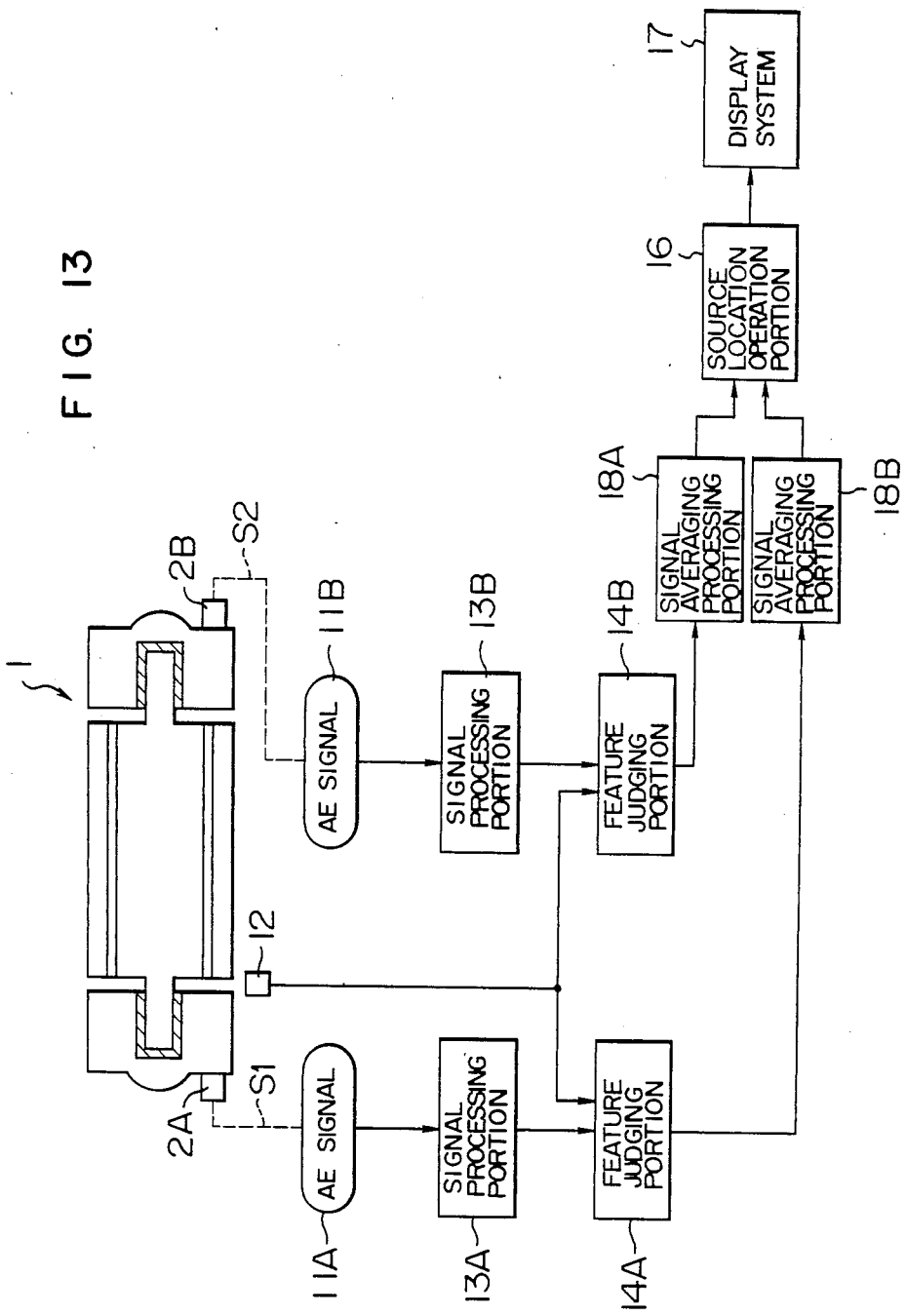

ROTATING MACHINERY DIAGNOSIS SYSTEM WITH ACOUSTIC EMISSION TECHNIQUE

BACKGROUND OF THE INVENTION

The present invention relates to a diagnosis system using an acoustic emission technique (hereinafter abbreviated to "AE technique"), and more particularly, relates to a rotating machinery diagnosis system with an AE technique, which has a function for judging factors causing mechanical abnormality of a rotary machine.

Accidents happening during the operation of rotary machines, such as steam turbines, electric generators, water turbines, rolling mills, and so on, are likely to lead to serious affairs. Particularly, mechanical accidents of rotating parts are dangerous. In order to prevent such accidents from occurring, it is necessary to detect abnormality in its early stages.

AE techniques have been proposed as one of means for detecting abnormality in its early stages. According to these AE techniques, an ultrasonic signal is detected by an AE sensor mounted on a part of a rotary machine and subject to signal processing. For example, as a method of rubbing monitoring, abnormality is detected through the process that the detected ultrasonic signal is passed through a filter to obtain a rotational component of the signal after the signal has been subject to envelope detection-processing, as disclosed, for example, in U.S. Pat. No. 4,478,082. Another example of the AE techniques is known as diagnosis of journal bearing damage, as disclosed in U.S. Pat. No. 4,481,819.

The prior art abnormality detection systems are useful in detecting abnormal conditions one by one. However, the prior type systems are not useful in detecting a plurality of kinds of abnormality.

SUMMARY OF THE INVENTION

An object of the present invention is therefore to provide a rotating machinery diagnosis system with an AE technique, which can detect (or judge) a plurality of kinds of abnormality occurring during the operation of a rotary machine.

The present invention is characterized in that the feature of an envelope-detected AE signal are analyzed by use of a computer to thereby classify abnormality on the basis of the result of analysis.

BRIEF DESCRIPTION OF THE DRAWINGS

FIG. 13 is a diagram showing a further embodiment of the present invention different from that of FIG. 11, arranged to detect a position where continuous type abnormality occurs unlike the embodiment of FIG. 13.

DESCRIPTION OF THE PREFERRED EMBODIMENTS

Figure 1:
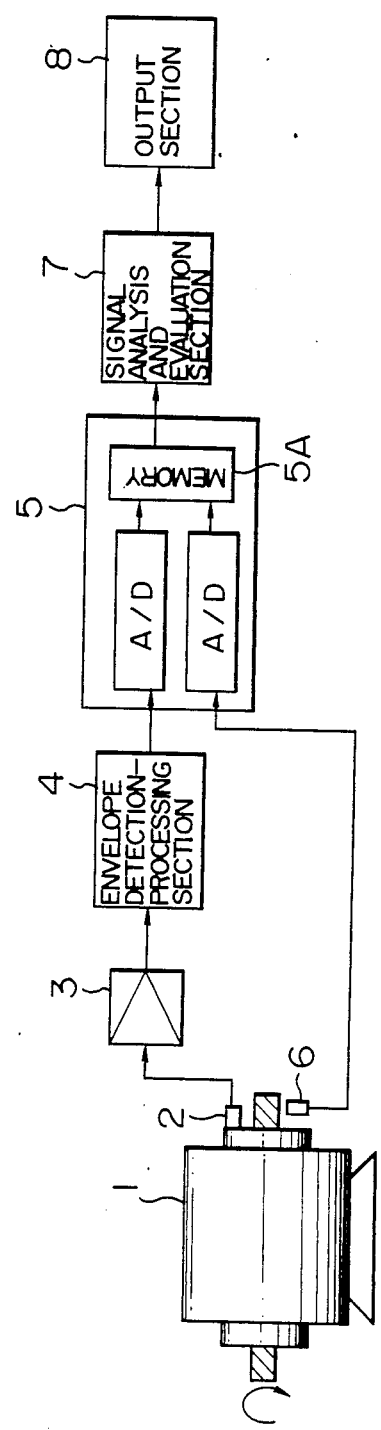
FIG. 1 is a block diagram showing an embodiment of the system according to the present invention.

Referring to FIG. 1, there is shown a diagram of a rotating machinery diagnosis system with an AE technique as an embodiment of the present invention. According to this embodiment, abnormality can be classified into those of the continuous type (abnormality due to mechanical contact of a rotor with a stator) and of the burst type (abnormality due to exfoliation and/or cracking of the rotor and stator). In FIG. 1, the output voltage of a known AE sensor 2 mounted on a rotary machine 1 is amplified by an amplifier 3 and the resulting voltage is detected by an envelope detection-processing section 4. The thus detected analog signal is converted into a digital signal by a signal converting and fetching section 5 whereafter the digital signal is stored in a storage. The signal converting and fetching section 5 is constituted by an analog-to-digital converting circuit, and arranged, for example when the revolutional speed of the rotary machine 1 is one per second, to keep on fetching the signal every one millisecond for about 16 seconds. Alternatively, the envelope detection-processing may be performed by means of software after the output signal of the amplifier 3 has converted into a digital signal and the digital signal has been fetched. In this case, the envelope detection-processing section 4 provided to follow the amplifier 3 becomes useless.

Figure 2:
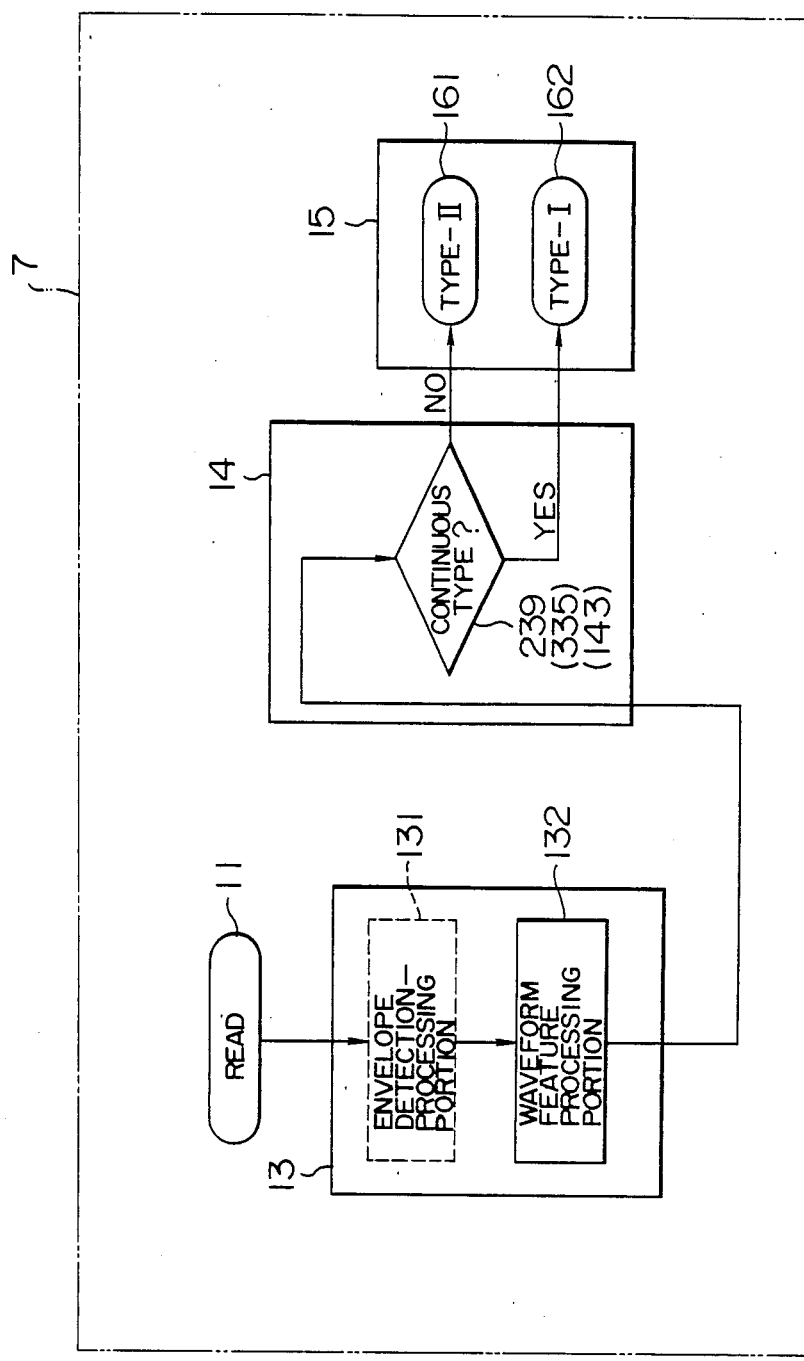
FIG. 2 is a flowchart for explaining the operation of a signal analysis and evaluation section in the embodiment.

On the other hand, a signal from a known rotation signal detecting portion 6 is also applied to the signal converting and fetching section 5, where the signal is converted into a digital signal at the same sampling frequency as described above, and the digital signal is stored in the memory 5A. The output signal of the signal converting and fetching section 5 is applied to a signal analysis and evaluation section 7, where the signal is processed in the manner as shown in the flowchart of FIG. 2, and the result is transmitted to an output section 8 including a display unit. The signal analysis and evaluation section 7 is constituted by a digital computer. FIG. 2 shows the operation of the signal analysis and evaluation section 7.

A way of thinking to be the basis of this diagnostic operation will be described hereunder with reference to Table 1. The contents of Table 1 have been found by the inventors of this application after repetition of long-time experiments.

TABLE 1

| Waveform Characteristics | |
| --- | --- |
| Continuous Type | Burst Type |
| Phenomenon due to mechanical contact of a rotor with a stator. (Type-I) | Phenomenon due to exfoliation/cracking of a rotor and a stator. (Type-II) |

As shown in Table 1, the cause of abnormality in the rotary machine is determined to be of either the type-I or the type-II on the basis of the fact whether the envelope-detected AE signal fetched by the signal converting and fetching section 5 of FIG. 1 is of the continuous type or of the burst type. Typical examples of the continuous type and burst type waveforms are shown in (A) and (B) of FIG. 3, respectively.

The diagnostic operation based on the above-mentioned way of thinking will be described in detail hereunder with reference to FIG. 2.

The data fetched for a predetermined time, for example, for a time of 16 seconds, and stored in the memory 5A as described in FIG. 1, are read out at the step 11 of FIG. 2 and processed on the basis of Table 1 through processing sections which are functionally categorized into a signal processing section 13, a feature deciding section 14 and a diagnostic output section 15. After the respective AE signal is processed by a waveform feature processing portion 132 of the signal processing section 13, the signal is processed by the feature deciding section 14. In the case where envelope detection-processing is made by means of software as described above, the envelope detection-processing section 4 of FIG. 1 is replaced by the step 131 of FIG. 2. An example of the waveform feature processing portion 132 of the signal processing section 13 is shown in FIG. 4.

Figure 3:
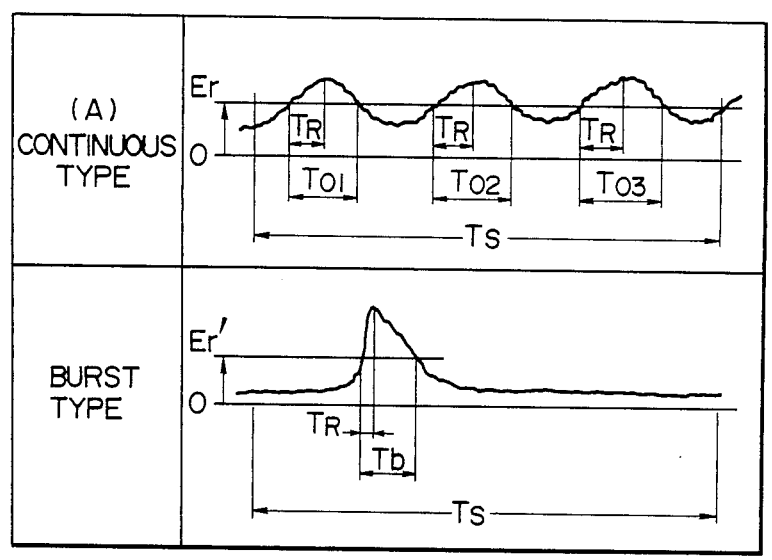
FIG. 3 is a diagram of waveforms of an acoustic signal generated due to abnormality of a rotary machine after the signal has been subject to detection processing.

There are various definitions for jugdement to determine whether the waveform is of the continuous type or the burst one. For example, it may be defined that a type having longer total duration of AE events in a predetermined time is the continuous type and a type having shorter total duration is the burst type. An example of each of the continuous type and burst type waveforms after envelope detection is shown in FIG. 3. When the waveform is cut off at a threshold Er, the upper portions represent duration TD1 to TDn. Judgement is made according to the size of total duration $\Sigma TD$ ($=TD1+TD2+\ldots+TDn$) within a predetermined time TS. The threshold Er may be selected to a predetermined fixed value or may be selected to a value a little higher than the average in the predetermined time ES.

Figure 4:
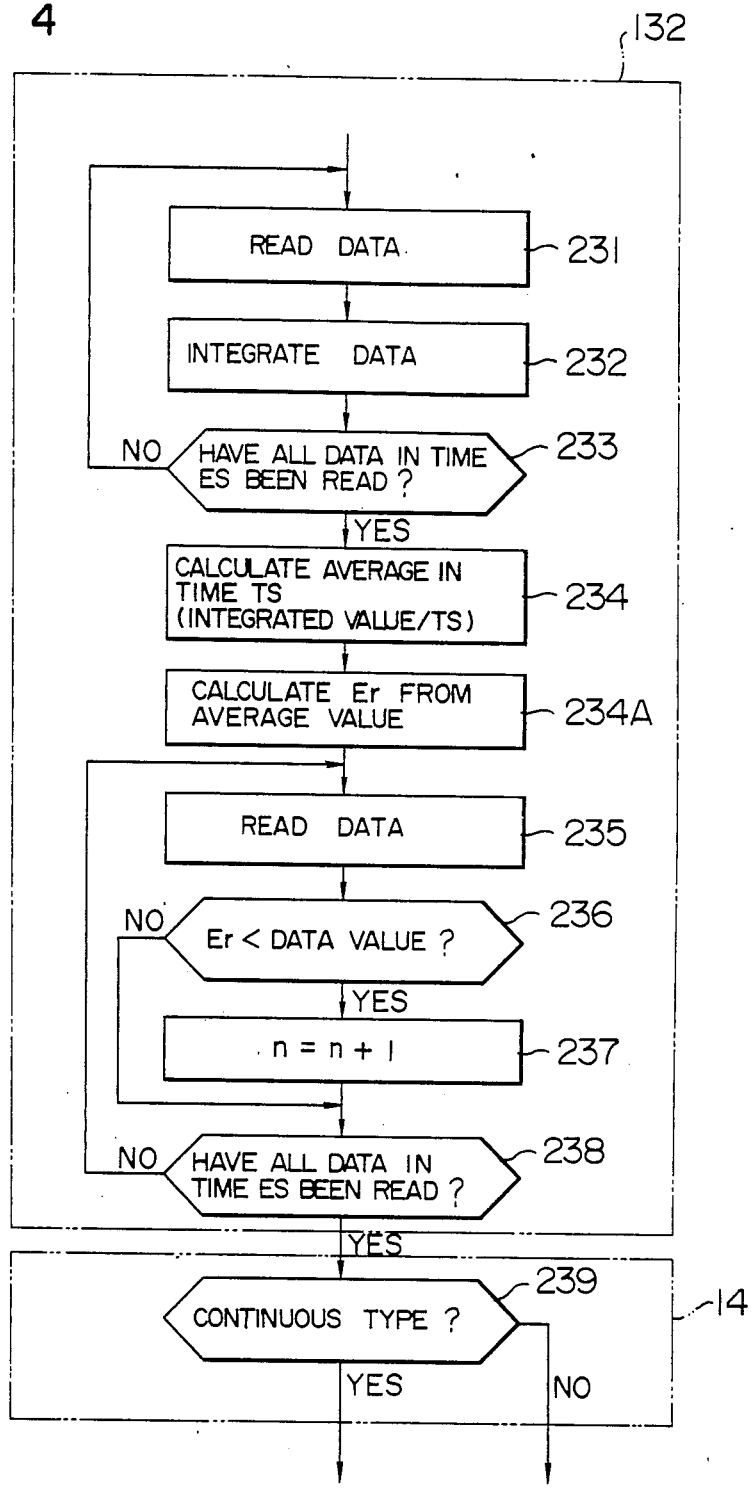
FIG. 4 is a flowchart for executing the operation of a waveform-feature processing section as shown in FIG. 2.

FIG. 4 is a flowchart showing the operation of the feature deciding section 14. The steps 231 to 234A are provided to determine the threshold Er. If a fixed value is used for the threshold, these steps become useless.

The data stored in the memory are read out in the step 231 and integrated in the step 232. Whether the integration in the predetermined time ES as described above has been completed or not is judged in the step 233, and if the result of judgement proves that the integration in the predetermined time ES has not yet completed the above-mentioned operations of reading and integrating of data are repeated in the steps 231 and 232. The predetermined time ES may be equal to the above-mentioned predetermined time TS. The judgement in the step 233 proves that the integration of data in the predetermined time ES has been completed, an average value of the integrated data in the predetermined time ES is calculated in the step 234. For example, the calculation is may be performed, for example, by dividing the integrated value by the number of sampling operations corresponding to the time ES (in the step 234). A value obtained by adding a predetermined value to the quatient of the above-mentioned division is used as the threshold Er (in the step 234A). The reason why it is preferable to use a value a little larger than the average as the threshold Er is that the output of the AE sensor is almost zero in normal conditions, that is, the average becomes almost zero, and, if the threshold is set to be equal to the average, the threshold also becomes almost zero so that the operations become apt to be affected by noises. The steps 234 to 238 are provided to calculate the total duration $\Sigma TD$ as described above. The data are read again out from the memory 5A in the step 235 and compared with the threshold in the step 236. If the value of the read-out data is larger than the threshold, the count number n is incremented by one. The count number n represents the number of times of sampling operations in which the sampled value of data larger than the threshold Er is entered, of all the number of times of data sampling operations. For example, assuming that the sampling frequency is fixed, it may be considered that the count number n represents the total duration $\Sigma TD$. When the judgement in the step 238 proves that the judgement in the step 236 as to all the data in the predetermined time ES has been completed, it can be determined that the count number n at that time represents the total duration $\Sigma TD$. When the count number n is larger than a predetermined number, it can be determined that the waveform feature is of the continuous type.

Figure 5:
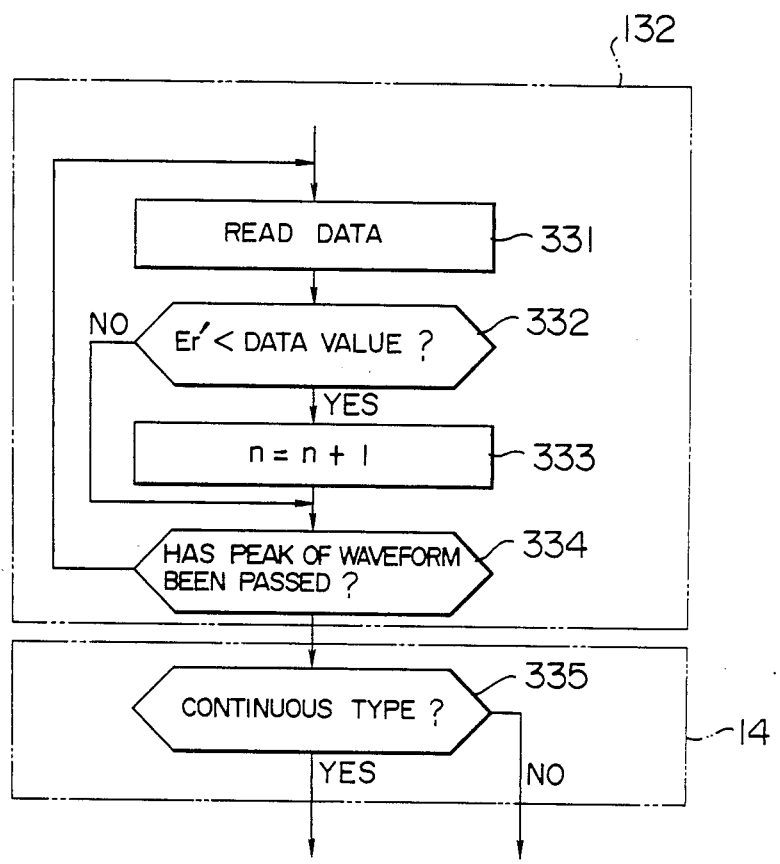
FIG. 5 is a flowchart for executing the operation of the waveform-feature processing section, shown as another embodiment different from that of FIG. 4.

FIG. 5 shows another embodiment of the feature deciding section 14, in which the peak value of the waveform is utilized. The steps 331 to 334 are provided to measure rising time TR as shown in FIG. 3. The data stored in the memory are read out in the step 331, and the sampled data are compared with a predetermined threshold Er' in the step 332. In the state where the value of the data is larger than the threshold Er', the count number n is incremented by one in the step 333. The count number n is established to represent the rising time TR of FIG. 3. The peak value of the waveform is detected in the step 334. One of known methods can be used for the detection of the peak value. The count number n upon the detection of the peak value represents the rising time TR of FIG. 3. In comparison between the time TR and a predetermined value, the judgement is made as to whether the waveform feature is of the continuous type or not in the step 335. When the time TR is larger than the predetermined value, it is determined in the step 335 that the feature is of the continuous type.

The feature deciding section 14 of FIG. 2 determines the signal feature on the basis of the result of the signal processing as shown in FIG. 4 or FIG. 5, and accordingly, judges whether the cause of abnormality is of the type-I or the type-II as shown in Table 1. Processing for the display of the cause of abnormality is made in the step 161 or 162 of FIG. 2 for the output section 8 of FIG. 1. Thus, a series of processing is completed.

Figure 6:
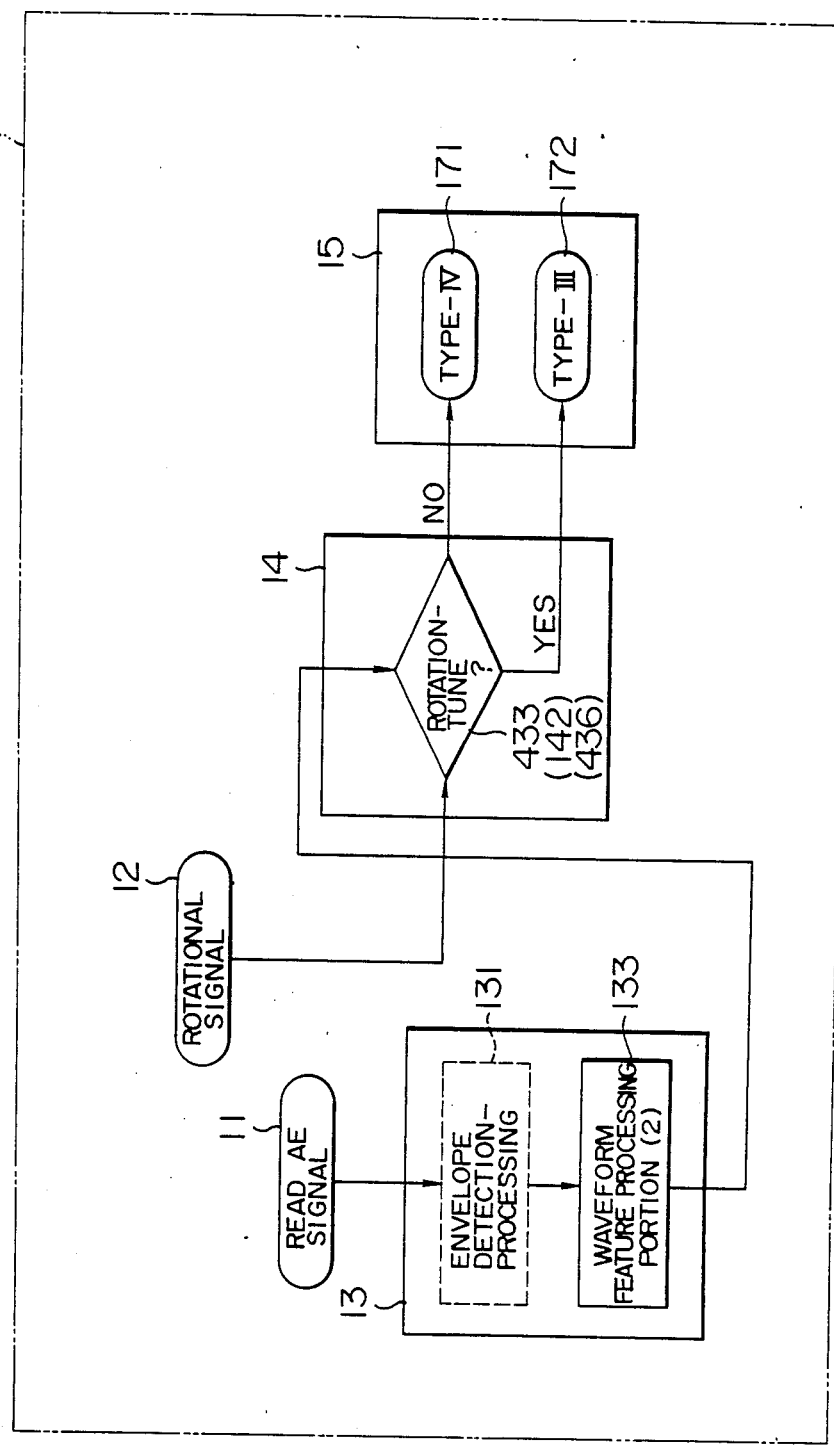
FIG. 6 is a flowchart for executing the operation of the signal analysis and evaluation section, shown as another embodiment different from that of FIG. 2.

FIG. 6 is a flowchart for executing a second embodiment of the present invention, in which it is possible to group the causes of abnormality into those of the rotation-synchronous type and of the rotation-asynchronous type.

Similarly to Table 1, Table 2 shows judging conditions which have been found by the inventors in this application after repetition of long-time experiments.

TABLE 2

| Frequency Characteristics | |
|---|---|
| Tuned Type | Unturned Type |
| Damage caused by a rotor. (Type-III) | Damage caused by a stator. (Type-IV) |

Figure 7:
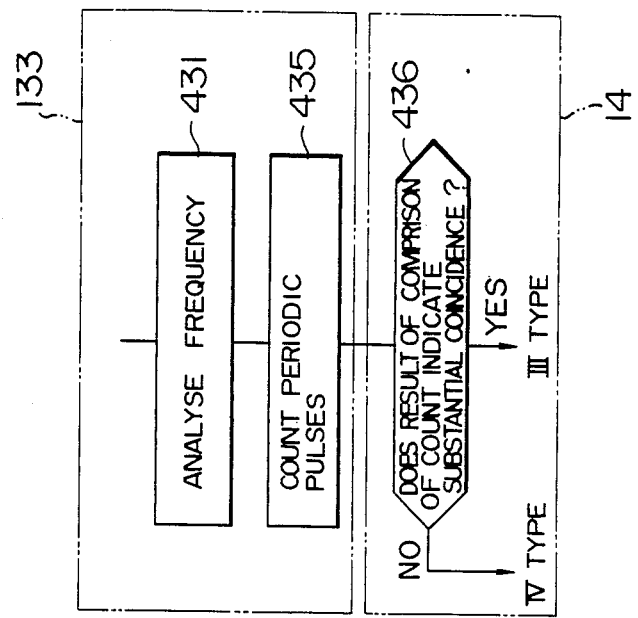
FIG. 7 is a flowchart for executing the operation of a waveform feature processing section as shown in FIG. 6.

Whether the cause of abnormality is of the type-III or the type-IV can be diagnosed by the fact whether the frequency characteristics is of the rotation tuned type or not. The diagnostic operation is shown in FIG. 6. Similarly to FIG. 2, FIG. 6 is a flowchart showing the operation of the signal analysis and estimation section 7 of FIG. 1. In the drawing, similarly to FIG. 2, processing sections are categorized into a signal processing section 13, a feature deciding section 14 and a diagnostic output section 15. The step 131 is provided for the same purpose as shown in FIG. 2. Processing for judging whether the cause is of the rotation tuned type or not as shown in Table 2 is made in the step 133 on the basis of the result of envelope detection. A specific example of the operation of the processing is shown in FIG. 7. With respect to fetching time, it is preferable to perform fetching operations for a period corresponding to at least five revolutions of the rotary machine. The output of envelope detection is frequency-analyzed in the step 431. Fundamentally, a technique known as an FFT (fast Fourier transformer) technique can be used for the frequency analysis. The FFT technique is described in a paper by J. A. Johnston, B. Eng., "Parallel Pipeline Fast Fourier Transformer", IEE PROCEEDING, VOL. 130, Part F, No. 6, October 1983.

In FIG. 6, the reference numeral 12 designates a step for reading the data from the rotation signal detector portion 6 of FIG. 1.

In FIG. 7, the frequency of the output signal of the envelope detection-processing portion is detected in the step 432 on the basis of the result of the frequency analysis. In the case where the detected frequency is almost equal to the rotational frequency of the rotor detected on the basis of the output of the rotation signal detector portion 6 of FIG. 1, it is decided that the signal is of the rotation-synchronous type in the step 433. Otherwise, the signal is determined to be of the untuned type.

Figure 8:
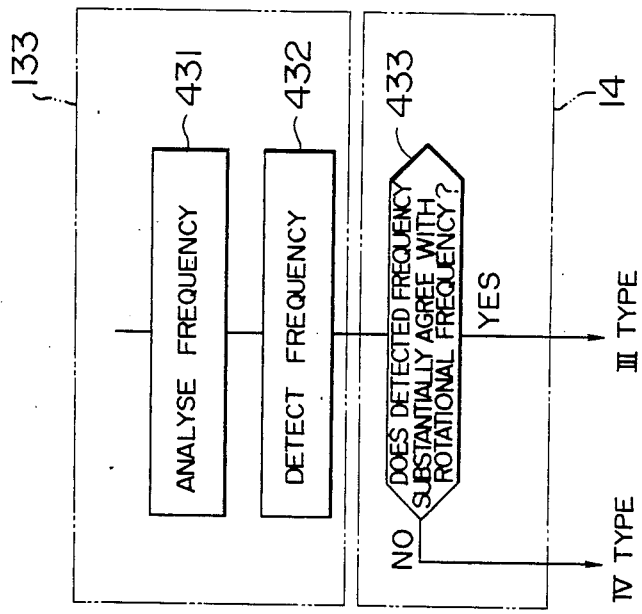
FIG. 8 is a flowchart for executing the operation of a waveform feature processing section, shown as another embodiment different from that of FIG. 7.

FIG. 8 shows an embodiment different from that of FIG. 7. The step 431 of FIG. 8 is almost equivalent to the step 431 of FIG. 7. The periodic pulses due to frequency analysis are counted in the step 435, and the signal is determined in the step 436 to be of the tuned type when this count number in the step 435 is equal to the count number of periodic pulses on the basis of the output of the rotation signal detector portion 6. On the basis of the judgement, the processing section 14 judges whether the cause of abnormality is of the type-IV type or of the type-III to thereby display the cause of abnormality.

While the operation of FIG. 2 or FIG. 6 has been described under the condition that abnormality exists, it is a matter of course that usual control is made almost under the normal condition. In the normal condition, the output of envelope detection becomes almost zero. In this case, it is a matter of course that indication of abnormality is not made.

While the two embodiments as described above with reference to FIGS. 2 and 6 show two kinds of diagnosis, combinations of the waveform analysis and frequency analysis shown in the embodiments make it possible to effect at least six kinds of diagnosis. Such an embodiment will be described on the basis of the flowchart of FIG. 9.

Table 3 shows the detail of diagnostic conditions which have been found by the inventors of this application after repetition of experiments.

TABLE 3

| Frequency Feature (Envelope-detected wave) | | Waveform Characteristics | |
|---|---|---|---|
| | | Continuous Type | Burst Type |
| Narrow Band Type | Tuned Type | A1 (Rubbing) | A2 (Rotor Crack) |
| | Untuned Type | B1 (Metal Wipe of Journal Bearing) | B2 (Metal Fatigue & Crack) |
| Wide Band Type | Untuned Type | C1 (Tilting of Journal Bearing) | C2 (Damage of Ball Bearing) |

Figure 9:
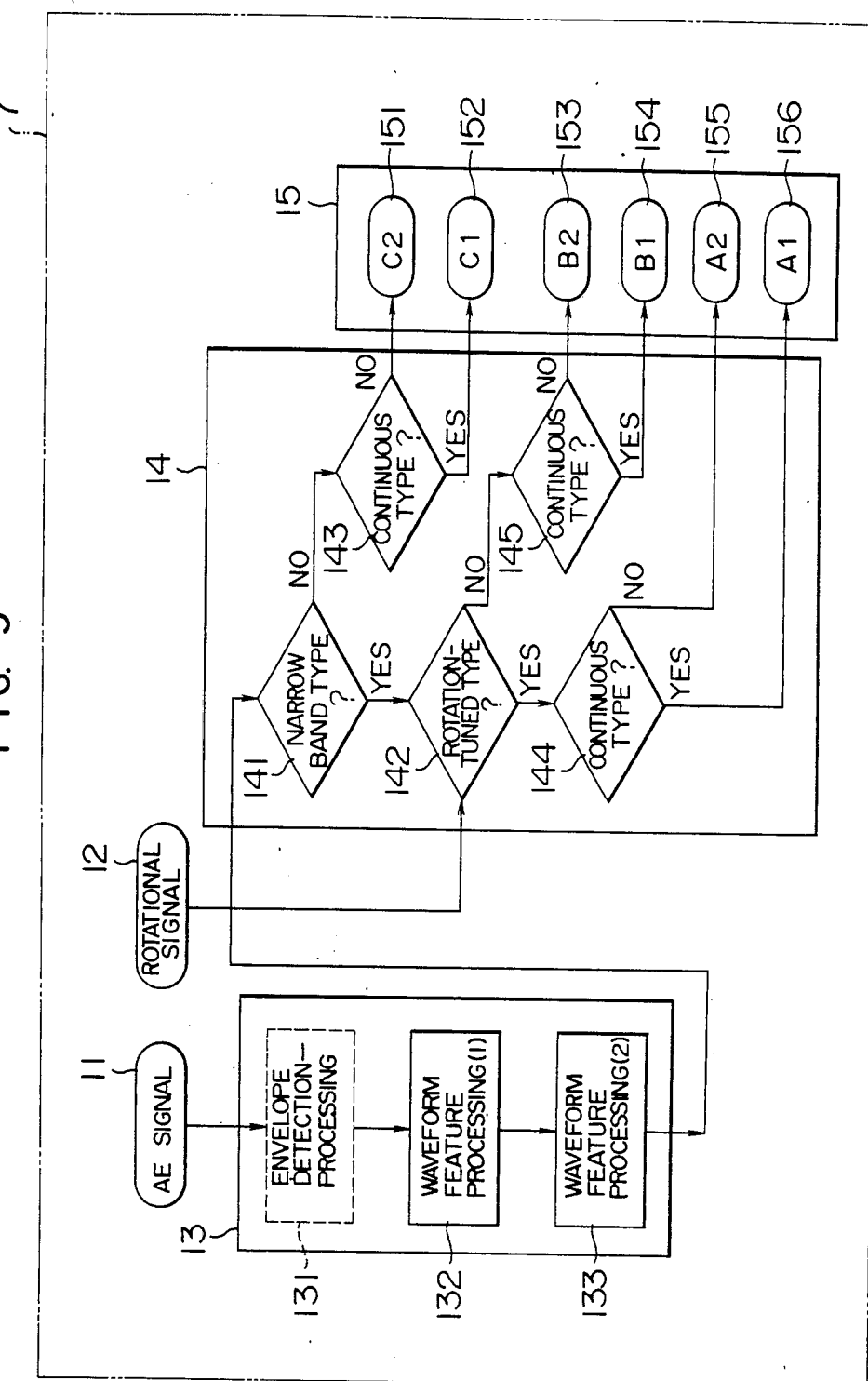
FIG. 9 is a flowchart for executing the operation of the signal analysis and evaluation section, shown as another embodiment different from those of FIGS. 2 and 6.

A flowchart of diagnosis on the basis of the diagnostic conditions of Table 3 is shown in FIG. 9.

A way of thinking to be the basis of this diagnostic operation will be described hereunder with reference to Table 3. Abnormality of a rotary machine can be classified by forms corresponding to the frequency feature and waveform feature of the envelope-detected AE signal. As shown in Table 3, the AE signal can be classified into those of the narrow band type and of the wide band type depending on the frequency feature, further classified into those of the rotation tuned type and of the untuned type depending on the rotational frequency components, and furthermore classified into those of the continuous type and of the burst type depending on the waveform feature. Consequently, the factors of abnormality can be classified into those of six types (A1, A2, B1, B2, C1, and C2).

The method of judging whether a factor of abnormality belongs to a narrow band type or a wide band type, will be described hereunder. For example, paying attention on a peak ratio of a maximum peak amplitude of FFT on the basis of the result of FFT, if the following expression is satisfied the factor of abnormality is of the narrow band type and otherwise of the wide band type:

$$A_P/\overline{A} \geq K_{fw}$$

where $A_P$ represents a maximum peak amplitude of FFT, $\overline{A}$ an average of amplitude of FFT, and $K_{fw}$ a constant for judging frequency band.

The factors causing abnormality, for example, such as bracketed in Table 3, can be discriminated.

The diagnostic operation based on the above-mentioned way of thinking will be described in detail hereunder with reference to FIG. 9. The operation is categorized by functions into a signal processing section 13, a feature deciding section 14 and a diagnostic output section 15. These sections are provided for the same purpose as shown in FIGS. 1 and 6. The envelope detection processing portion 131, the waveform feature processing portion 132 and the frequency feature processing portion 133 which constitute the AE signal processing section 13, operate in the same manner as those shown in FIGS. 1 and 6. Through the AE signal processing section 13, the signal is applied to the feature deciding section 14. On the basis of the result of operation in the AE signal processing section 13, the following judgement is made by the feature deciding section 14. In the section 14, judgement is made in the band type deciding step 141 as to whether the frequency feature is of the narrow band type or of the wide band type, and judgement is made in the rotation-synchronous type deciding step 142 as to whether the frequency feature is in synchronism with the rotation signal 12 or not. In the waveform deciding steps 143, 144 and 145, judgement is made as to whether the waveform feature is of the continuous type or of the burst type.

According to the judgement on the basis of FIG. 9, the output signal classified into six groups A1–C2 by factors causing abnormality can be produced at the diagnostic output section 15. The thus obtained output signal may be used to display the abnormality.

Figure 10:
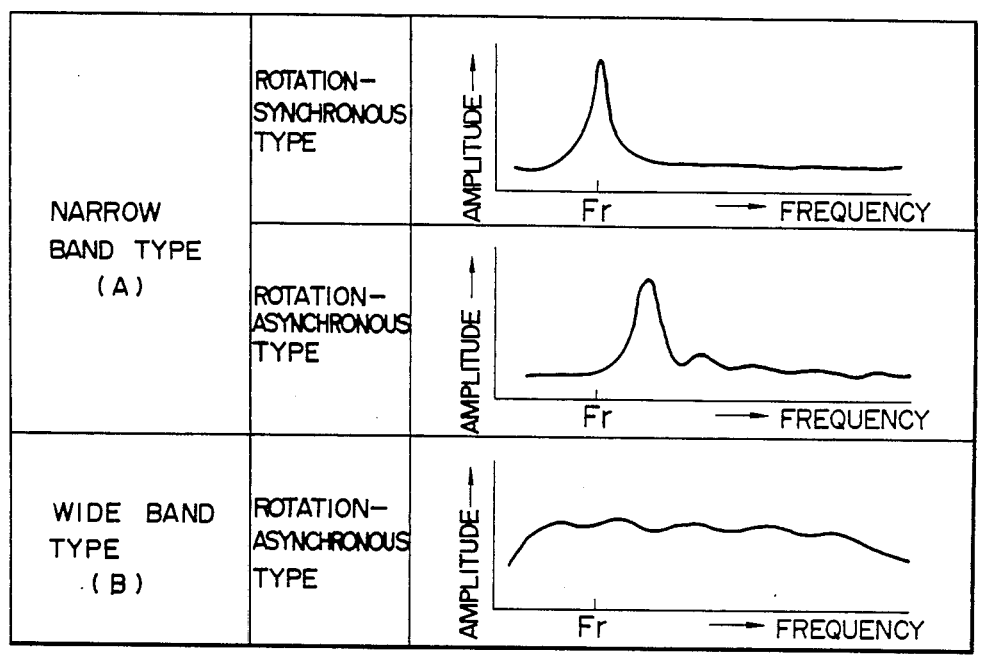
FIG. 10 is a diagram showing rotation-synchronous type and rotation-asynchronous type waveforms.

The judgement made in the waveform deciding step 143 as to whether the waveform is of the continuous type or of the burst type, is effected by using the result of operation performed in the waveform feature processing step 132 described with respect to FIG. 2. Any processor can be used for the operation to be made in the frequency feature processing step 133 of FIG. 6 so long as it has a frequency analyzing function. For example, the processing can be made in such a manner as described as to FIG. 6. An example of each of the frequency features classified by band types and rotation tuned types is shown in FIG. 10. In FIG. 10, Fr represents rotational frequency. The rotation-synchronous type is characterized in that the main component accords to Fr. Only in order to judge whether the frequency feature is of the wide band type or of the narrow band type, a known technique can be used here. For example, the judgement may be effected in such a manner as shown in FIG. 7 or 8 in which the signal is separated into frequency components and the judgement is made on the basis of the fact that the output of the frequency components ranges in a wide band or not.

The typical factors causing abnormality as shown in Table 3 will be described hereunder. An example of the type A1 is "rubbing". In the case of "rubbing", the signal is in synchronism with rotation because the strength of rubbing varies due to the eccentricity of rotation. As example of the type A2 is "rotor cracks". In the case where the rotor is cracked, stress reaches its maximum at a certain rotational angular position of the rotor because of the eccentricity of rotation of the rotor, and, accordingly, the crack is progressed to thereby generate a burst type AE signal synchronizrd with the rotation. An example of the type B1 is "metal wipe phenomenon of journal bearing". The metal wipe grows due to contact with metal on the failure of oil film supply to thereby generate lots of continuous type AEs in every rotation of a shaft. The AEs are characterized in that the AEs are periodic but not-synchronized with the rotational frequency. An example of the type B2 is "generation of cracks due to metal fatigue". An example of the type C1 is "phenomenon of damage due to tilting of journal bearing". Examples of the type C2 are "damage of ball bearing", "serious damage of slide bearing", etc.

Figure 11:
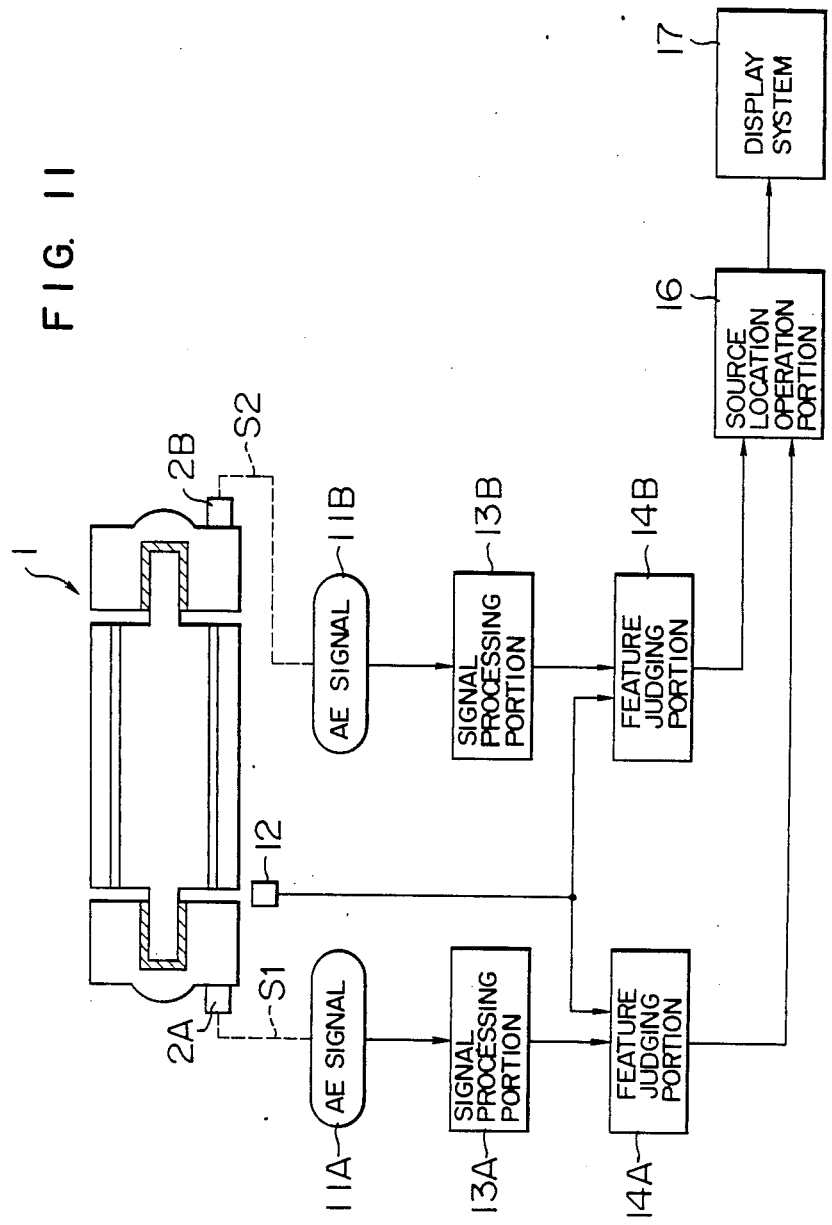
FIG. 11 is a diagram showing another embodiment of the present invention arranged to detect a position where burst type abnormality occurs.

Other embodiments of the present invention will be described hereunder. FIGS. 11 and 13 show diagnosis systems each of which is capable of detecting the position where abnormality occurs as well as capable of separating abnormality into groups. In each system, at least two series of AE sensors and diagnostic control systems are provided to detect the position on the basis of the time difference between AE signals. That is, one of the two series comprises an AE sensor 2A, an AE signal 11A, a signal processing section 13A (equivalent to the section 13 of FIG. 2), and a feature deciding section 14A (equivalent to the section 14 of FIG. 2). The other series comprises like portions or sections 2B, 11B, 13B and 14A. As described above, burst type abnormal conditions are judged by the feature deciding sections 14A and 14B, respectively. After the judgement, the position (where abnormality occurs) on the basis of the time difference is detected by a position detecting operation portion 16, and the output signal is transmitted to a display unit 17.

Figure 12:
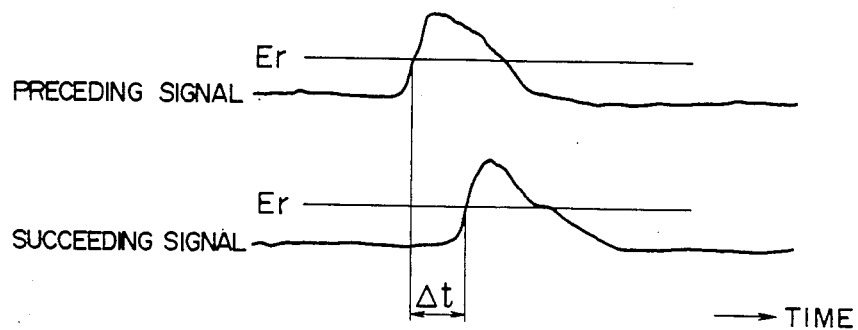
FIG. 12 is a diagram showing waveforms for explaining the operation of the system of FIG. 11.
Figure 14:
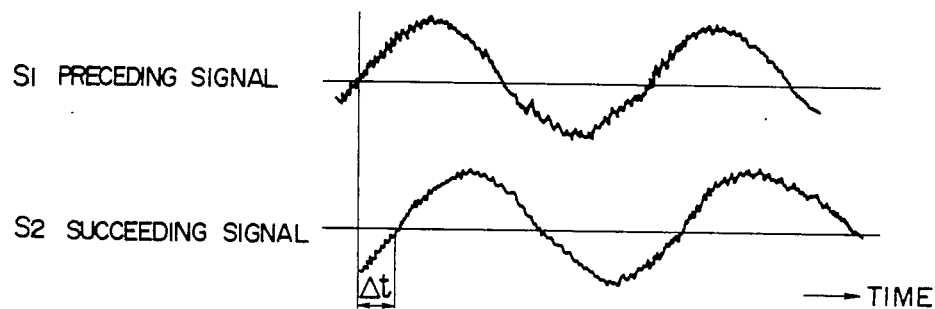
FIG. 14 is a diagram of waveforms for explaining the operation of the system of FIG. 13.

The embodiment of FIG. 11 shows the process for detecting the position of abnormality generation source in the case where the AE signal is concluded to be of the burst type. As shown in FIG. 12, the time difference between two signals S1 and S2 from the respective AE sensors 2A and 2B is measured. The position of abnormality generation source can be computed as the distance L from the center according to the following equation:

$$L = v \cdot \Delta t / 2 \tag{1}$$

where v represents the velocity of sound and $\Delta t$ is the time difference.

FIG. 13 shows another embodiment capable of detecting the source position of abnormality similarly to FIG. 11. FIG. 13 shows, however, the process for detecting the position of abnormality generation source in the case where the AE signal is concluded to be of the continuous type instead of the burst type shown in FIG. 11. In FIG. 13, items the same as or similar to those FIG. 11 are correspondingly referenced. The embodiment of FIG. 13 is different from that of FIG. 11 in that the position detection of FIG. 13 is made after rotation tuned signals are processed by arithmetical mean processing sections 18a and 18b in order to improve accuracy in position detection. Particularly, in the case of rotation tuned signals, the accuracy in position detection can be improved by the arithmetical mean processing.

The evaluation for the source location of abnormality in the embodiments of FIGS. 11 and 13 is disclosed in above-mentioned U.S. Pat. No. 4,478,082, and hence, the detailed description thereof will be omitted here.

According to the present invention, it is possible to detect a plurality of kinds of factors causing abnormality, such as damage or crack of the rotary machine, which may develop into a serious affair.

We claim:

1. A rotating machinery diagnosis system with an AE technique, comprising:
   an AE sensor mounted on a rotary machine for sensing an acoustic signal of said rotary machine;
   envelope detector means for obtaining an envelope signal from the acoustic signal from said AE sensor;
   waveform-feature processor means for performing signal processing so as to detect a feature of waveform of an output waveform signal from said envelope detector means;
   feature decision means for judging whether said feature of waveform belongs to a continuous type or a burst type on the basis of an output signal from said waveform-feature processor means; and diagnostic output means for outputting and displaying an output signal from said feature decision means.

2. A system according to claim 1, in which said waveform-feature processor means includes means for calculating an average of said waveform signal in a predetermined time, means for calculating a threshold on the basis of said average, and means for calculating a sum of time in the case where said waveform signal exceeds said threshold within said predetermined time.

3. A system according to claim 1, in which said waveform-feature processor means includes means for detecting time after said waveform signal exceeds a predetermined threshold till said waveform signal reaches a peak value of the waveform thereof.

4. A rotating machinery diagnosis system with an AE technique, comprising:

an AE sensor mounted on a rotary machine for sensing an acoustic signal generated in said rotary machine;

a detection portion mounted on said rotary machine for detecting a rotation signal of said rotary machine;

envelope detector means for obtaining an envelope signal from the acoustic signal from said AE sensor;

waveform-feature processor means for performing signal processing so as to detect a feature of waveform of an output waveform signal from said envelope detector means;

feature decision means for judging whether said feature of waveform belongs to a rotation-synchronous type or a rotation-asynchronous type on the basis of an output signal from said waveform-feature processor means and an output from said detection portion; and diagnostic output means for outputting and displaying an output signal from said feature decision means.

5. A system according to claim 4, in which said waveform-feature processor means includes means for analyzing the frequency of said waveform signal, and means for detecting the frequency of said waveform signal.

6. A system according to claim 4, in which said waveform-feature processor means includes means for analyzing the frequency of said waveform signal, and means for counting frequency pulses.

7. A rotating machinery diagnosis system with an AE technique, comprising:

an AE sensor mounted on a rotary machine for sensing an acoustic signal of said rotary machine;

a detection portion mounted on said rotary machine for detecting a rotation signal of said rotary machine;

envelope detector means for obtaining an envelope signal from the acoustic signal from said AE sensor;

waveform-feature processor means for performing signal processing so as to detect a feature of waveform of an output waveform signal from said envelope detector means;

feature decision means for judging whether said feature of waveform belongs to a narrow band type or a wide band type, to a rotation-synchronous type or a rotation-asynchronous type, and to a continuous type or a non-continuous type, on the basis of an output signal from said waveform-feature processor means and an output from said detection portion; and diagnostic output means for outputting and displaying an output signal from said feature decision means.

8. A rotating machinery diagnosis system with an AE technique, comprising:

a first AE sensor mounted on a rotary machine for sensing an acoustic signal of said rotary machine;

first signal processor means including first envelope detector means for obtaining an envelope signal from said acoustic signal from said first AE sensor, and first waveform-feature processor means for performing signal processing so as to detect a feature of waveform of an output waveform signal from said first envelope detector means;

first feature decision means for detecting that the feature of waveform of said output waveform signal from said first envelope detector means belongs to a burst type on the basis of an output signal from said first signal processor means;

a second AE sensor mounted on a rotary machine for sensing an acoustic signal of said rotary machine;

second signal processor means including second envelope detector means for obtaining an envelope signal from said acoustic signal from said second AE sensor, and second waveform-feature processor means for performing signal processing so as to detect a feature of waveform of an output waveform signal from said second envelope detector means;

second feature decision means for detecting that the feature of waveform of said output waveform signal from said second envelope detector means belongs to a continuous type on the basis of an output signal from said second signal processor means;

a position detection operation portion for detecting a position where burst type abnormality is generated on the basis of respective output signals from said first and second feature decision means; and means for displaying the position where said abnormality is generated.

9. A rotating machinery diagnosis system with an AE technique, comprising:

a first AE sensor mounted on a rotary machine for sensing an acoustic signal of said rotary machine;

first signal processor means including first envelope detector means for obtaining an envelope signal from said acoustic signal from said first AE sensor, and first waveform-feature processor means for performing signal processing so as to detect a feature of waveform of an output waveform signal from sa.id first envelope detector means;

first feature decision means for detecting that the feature of waveform of said output waveform signal from said first envelope detector means belongs to a burst type on the basis of an output signal from said first signal processor means;

a second AE sensor mounted on a rotary machine for sensing an acoustic signal of said rotary machine;

second signal processor means including second envelope detector means for obtaining an envelope signal from said acoustic signal from said second AE sensor, and second waveform-feature processor means for performing signal processing so as to detect a feature of waveform of an output waveform signal from said second envelope detector means;

second feature decision means for detecting that the feature of waveform of said output waveform signal from said second envelope detector means belongs to a burst type on the basis of an output signal from said second signal processor means;

first and second arithmetical average processor means for performing arithmetical average processing with respect to respective output signals from said first and second feature decision means;

a position evaluation operation portion for determining a position where continuous type abnormality is generated, on the basis of respective output signals from said first and second arithmetical average processor means; and means for displaying the position where said abnormality is generated.

* * * * *